US007518004B2

(12) United States Patent
Mueller et al.

(10) Patent No.: US 7,518,004 B2
(45) Date of Patent: Apr. 14, 2009

(54) METHOD FOR REACTING AN ORGANIC COMPOUND WITH A HYDROPEROXIDE

(75) Inventors: Ulrich Mueller, Neustadt (DE); Peter Bassler, Viernheim (DE); Joaquim Henrique Teles, Otterstadt (DE); Norbert Rieber, Mannheim (DE)

(73) Assignee: BASF Aktiengesellschaft, Ludwigshafen (DE)

( * ) Notice: Subject to any disclaimer, the term of this patent is extended or adjusted under 35 U.S.C. 154(b) by 409 days.

(21) Appl. No.: 10/555,985

(22) PCT Filed: May 10, 2004

(86) PCT No.: PCT/EP2004/004973

§ 371 (c)(1),
(2), (4) Date: Nov. 8, 2005

(87) PCT Pub. No.: WO2004/098769

PCT Pub. Date: Nov. 18, 2004

(65) Prior Publication Data

US 2006/0217576 A1 Sep. 28, 2006

(30) Foreign Application Priority Data

May 8, 2003 (DE) ................. 103 20 634

(51) Int. Cl.
*C07D 301/19* (2006.01)
(52) U.S. Cl. ..................................... 549/529
(58) Field of Classification Search .............. 549/529
See application file for complete search history.

(56) References Cited

U.S. PATENT DOCUMENTS 4,547,602 A 10/1985 Tabak
4,861,932 A 8/1989 Chen et al.

FOREIGN PATENT DOCUMENTS

| DE | 198 35 907 | 2/2000 |
|---|---|---|
| DE | 102 32 406 | 1/2004 |
| EP | 0 311 983 | 4/1989 |
| EP | 0 200 260 | 5/1990 |
| EP | 0 389 041 | 9/1990 |
| EP | 0 405 978 | 1/1991 |
| EP | 0 883 439 | 12/1998 |
| WO | 94 02245 | 2/1994 |
| WO | 95 19222 | 7/1995 |
| WO | 98 55228 | 12/1998 |
| WO | 98 55229 | 12/1998 |
| WO | WO 99/01445 | 1/1999 |
| WO | 00 07965 | 2/2000 |
| WO | 01 10855 | 2/2001 |
| WO | 01 72729 | 10/2001 |
| WO | 02 08214 | 1/2002 |
| WO | 02 28774 | 4/2002 |

OTHER PUBLICATIONS

Wu et al. "Hydrothermal Synthesis of a Novel Titanosilicate with MWW Topology", Chemistry Letters, pp. 774-775 2000.
Baerlocher et al., Atlas of Zeolite Framework Types, 5th edition, pp. 202-203.

*Primary Examiner*—Jafar Parsa
(74) *Attorney, Agent, or Firm*—Oblon, Spivak, McClelland, Maier & Neustadt, P.C.

(57) ABSTRACT

Process for the catalyzed reaction of an organic compound with a hydroperoxide in at least one reactor using at least two different zeolite catalysts, wherein at least two of the different zeolite catalysts are used physically separately from one another.

20 Claims, No Drawings

METHOD FOR REACTING AN ORGANIC COMPOUND WITH A HYDROPEROXIDE

The present invention relates to a process for reacting an organic compound with a hydroperoxide, in which at least two different titanium zeolite catalysts are used. At least two of the different catalysts are physically separated from one another, for example by the different catalysts being located in different reactors which are connected in series or being located in a single reactor and being physically separated from one another in this reactor.

The reaction of organic compounds with hydroperoxides is treated in numerous documents of the prior art. However, these generally discuss only processes in which a single catalyst is used for the reaction of the organic compound with a hydroperoxide.

WO 00/07965 by the applicant relates, for example, to a process for reacting an organic compound with a hydroperoxide, in which it is cursorily mentioned, inter alia, that one or more suitable catalysts can be added to improve the efficiency of this reaction. However, WO 00/07965 gives no further information as to how a process in which more than one catalyst is used could be configured. Accordingly, the explicitly described embodiments of this document relate to a process in which the organic compound is brought into contact with one heterogeneous catalyst.

WO 01/72729 by the applicant likewise relates to a process for reacting an organic compound with a hydroperoxide, which is directed at very efficient regeneration of the catalyst. In this context, it describes, inter alia, embodiments in which, apart from the necessary presence of at least two parallel reactors, at least two reactors are connected in series. In this process, catalysts of the same type but of differing reactivity can be present in different parallel reactors. WO 1/72729 gives no information about differing catalysts.

WO 01/10855 by the applicant likewise concerns a process for reacting an organic compound with a hydroperoxide, in which inhomogeneous reaction conditions are generated. In the process described there, both the pH and the temperature and possibly also the pressure are altered in the reaction medium. WO 01/10855 makes no reference to a variation of the catalyst used in the process.

The present invention accordingly provides a process for the catalyzed reaction of an organic compound with a hydroperoxide in at least one reactor using at least two different zeolite catalysts, wherein at least two of the different zeolite catalysts are used physically separated from one another.

Zeolite catalysts used in the process of the present invention can either be the zeolitic material itself or shaped bodies produced from the zeolitic material or mixtures of zeolitic material as such and shaped bodies produced from the zeolitic material. The term "different zeolite catalysts" as used in the context of the present invention can therefore relate to differences between zeolitic materials and also to differences in respect of the properties of the shaped bodies.

Differences in respect of the zeolitic materials are, for example,
- the titanium content of the zeolitic material;
- the content of chemical elements other than titanium;
- the porosity of the zeolite, with the porosity differing, for example, in terms of the geometry of the pores of the different zeolite catalysts and these accordingly having, for example, differing pore volumes, differing pore diameters or differing surface areas of the pores; the zeolites can likewise differ in respect of the pore distribution;
- the crystal structure of the zeolitic material;
- the surface modification of the zeolitic material;
- the acidity of the zeolitic material.

Differences in respect of the shaped bodies are, for example,
- the geometry of the shaped catalyst bodies;
- the porosity of the shaped bodies, with the porosity differing, for example, in terms of the geometry of the pores of the different shaped bodies and these accordingly having, for example, differing pore volumes, differing pore diameters or differing surface areas of the pores; the shaped bodies can likewise differ in respect of the pore distribution;
- the mechanical strength of the shaped bodies;
- the binder content of the shaped catalyst bodies;
- the type of binder material used for producing the shaped catalyst bodies;
- the content of catalytically active zeolitic material in the shaped catalyst bodies;
- the carbon content of the shaped bodies.

For the purposes of the present invention, the term "different zeolite catalysts" also encompasses two catalyst mixtures which differ from one another and which can each comprise at least two different shaped bodies or at least two different zeolitic materials as such or at least one shaped body and at least one zeolitic material as such. Different catalyst mixtures are thus mixtures as described above which differ in terms of either
- at least one of the distinguishing features described above by way of example for the zeolitic material or the shaped bodies,
- or the mixing ratio of the components present in the mixture
- or both at least one of the distinguishing features described above by way of example for the zeolitic material or the shaped bodies and also the mixing ratio of the components present in the mixture.

The term "physically separately" as used for the purposes of the present invention refers to embodiments in which the apparatus in which the reaction is carried out has at least two compartments of which one contains a zeolite catalyst and at least one other compartment contains at least one further zeolite catalyst which differs from the zeolite catalyst present in the first compartment.

Such compartmentalization can, for example, be realized in a single reactor, with various embodiments of the compartmentalization once again being possible.

Thus, the compartmentalization can, for example, be achieved in a single reactor by two or more different zones of the reactor being provided with different zeolite catalysts. Here, the different zones of the reactor can be separated from one another by means of at least one mechanical separation device so as to physically separate the different zeolite catalysts. Accordingly, one or more identical or different mechanical separation devices can be provided between two zones. In the case of three or more zones, the same or different separation devices can be provided for separating the various zones.

Examples of mechanical separation devices are sieve plates such as sheet-metal sieve plates or mesh plates and ordered packing or packing element knitteds as used, for example, in distillation columns, which according to a particularly preferred embodiment of the process of the present invention are used when the catalysts are used as shaped bodies. Thus, for example, if shaped catalyst bodies of a first geometry are used in a first zone, shaped catalyst bodies of a second geometry are used in a second zone and shaped catalyst bodies of a third geometry are used in a third zone, the sieve plates which are, for example, preferably used for separating the zones can differ in their mesh opening which can be matched to the geometry of the respective shaped bodies.

Likewise, the materials of which the mechanical separation devices are made can differ from one another.

Accordingly, the present invention also provides a process as described above in which the different catalysts are physically separated from one another by means of at least one mechanical separation device.

The compartmentalization according to the present invention in a single reactor can also be realized without additional mechanical separation devices. This is possible, for example, by means of a special configuration of the interior wall or walls of the reactor which have, for example, spaced depressions, recesses or similar configurations in which the different catalysts can be accommodated.

In achieving the compartmentalization according to the present invention, it is likewise possible for the individual compartments containing the different zeolite catalysts to adjoin one another directly without there being a spacing between the different zeolite catalysts. It is thus possible to equip the reactor with a first zeolite catalyst in a first zone and a second zeolite catalyst which differs from the first zeolite catalyst in a directly adjoining second zone, with the two catalyst zones having one or more shared interfaces. At the interface between the two zones, mixing of the two different zeolite catalysts can occur, as long as it is ensured that there is an inhomogeneity in the zeolite catalyst distribution over the two zones. For the purposes of the present invention, this term "inhomogeneity in the zeolite catalyst distribution" refers to a configuration in which at least part of the first zone consists predominantly, preferably exclusively, of the first zeolite catalyst and at least part of the second zone consists predominantly, preferably exclusively, of the second zeolite catalyst.

In a particularly preferred embodiment, this is achieved, for example, by means of a structured bed of different catalysts. A first zone of the reactor is in this case provided by a bed of a first zeolite catalyst which represents the first catalyst compartment. A second zone of the reactor is subsequently produced by pouring the second zeolite catalyst, which differs from the first, onto the first compartment to form a second compartment. Likewise, a third compartment or further compartments can also be added, with a zeolite catalyst which is different from both the first catalysts or from one of the first two catalysts being able to be used in the third compartment or a further compartment. This way of producing catalyst zones is referred to as "a structured bed" for the purposes of the present invention.

Compared to conventional processes in which a reactor is equipped with only a single zeolite catalyst, this structured bed offers the advantage, inter alia, that targeted selection of the catalysts used in various reactor zones enables, for example, the conversion in the reaction to be influenced in a positive way. For example, in a continuous process in which the reactants hydroperoxide and organic compound are conveyed through the reactor and pass through the various reactor zones provided with the different zeolite catalysts, the individual catalysts can be matched to the progress of the reaction.

It is thus possible, for example, to choose the zeolite catalyst in a first zone of the reactor in which the concentration of unreacted reactants is high in such a way that the conversion, for example in an exothermic reaction, is just so high that the heat evolved can still be removed. In a next reactor zone in which the concentration of the reactants is lower, it is then possible to use a zeolite catalyst which achieves, for example, a higher conversion, i.e. is more active in respect of the reaction. The inhomogeneity in the concentrations of the reactants hydroperoxide and organic compound as they pass through the reactor and the resulting inhomogeneity in the reaction mixture comprising the reactants hydroperoxide and organic compound and the reaction product or products formed therefrom can accordingly be compensated by appropriate selection of different zeolite catalysts and thus an inhomogeneity in, for example, the catalyst activity over the reactor.

For example, it is possible for the reaction of hydroperoxide with the organic compound to form products which are able to react further either with hydroperoxide or the organic compound or both with hydroperoxide and the organic compound to form an undesirable downstream product. In this case, the concentration of desired product and thus the probability of undesirable downstream product being formed becomes ever greater as the reaction mixture passes through the reactor. Accordingly, it is possible, for example, to use a first zeolite catalyst in a first reactor zone and in a second reactor zone to use a different zeolite catalyst which still catalyzes the reaction of hydroperoxide and organic compound but is less active in respect of the further reaction to the undesirable downstream product than is the zeolite catalyst in the first reactor zone.

Preference is given, for example, to using a titanium zeolite catalyst having a high titanium content and accordingly a high activity in respect of the reaction of the organic compound with hydroperoxide in a first compartment of the reactor and a titanium zeolite catalyst having a lower titanium content than the first titanium zeolite catalyst in a second compartment of the reactor. In a more preferred embodiment, the two titanium zeolite catalysts have the same crystal structure. In a likewise preferred embodiment, the two titanium zeolite catalysts have different crystal structures, for example a crystal structure of the MFI type in the case of the catalyst in the first compartment and a crystal structure of the MWW type in the case of the catalyst in the second compartment. It is likewise possible for the catalyst in the first compartment to have a crystal structure of the MWW type and the catalyst in the second compartment to have a crystal structure of the MFI type. In these embodiments, particular preference is given to the reaction mixture firstly passing through the first compartment and subsequently passing through the second compartment on its way through the reactor.

Accordingly, the present invention also provides a process as described above in which the reaction of the organic compound is carried out in a single reactor.

The present invention likewise provides a reactor for the reaction of an organic compound with a hydroperoxide, comprising at least two physically separate, different zeolite catalysts.

The compartmentalization according to the present invention can also be achieved, for example, by use of at least two reactors connected in series, with at least one zeolite catalyst being used for the reaction in a first reactor and at least one further zeolite catalyst which differs from the zeolite catalyst used in the first reactor being used for the reaction in at least one further reactor.

In this embodiment, it is possible, for example, to use a first catalyst in at least one first reactor and in at least one second reactor to use a second catalyst different from the first catalyst, with the catalyst in the first reactor being able to be, for example, in the form of zeolitic material or shaped bodies or a mixture of zeolitic material and shaped bodies and the catalyst in the second reactor being able to be in the form of zeolitic material or shaped bodies or a mixture of zeolitic material and shaped bodies.

Likewise, the catalyst can, for example, be used as a mesh catalyst based on inert woven meshes such as inert woven meshes made of metals, plastics, aluminum oxides, glass fibers, carbon fibers and/or graphite. Based on the weight of the zeolite catalyst, such mesh catalysts preferably have an alkali metal content of less than 500 ppm. These mesh catalysts are preferably produced by a process in which at least one zeolite, preferably at least one titanium zeolite, is crystallized onto an inert woven mesh. Mesh catalysts of this type and ways of producing them are described in EP 0 883 439 B1, whose relevant contents are fully incorporated by reference into the disclosure of the present invention.

Accordingly, the present invention also provides an assembly of reactors connected in series for the reaction of an organic compound with a hydroperoxide, which comprises at least two reactors and in which at least two reactors contain different zeolite catalysts.

Regardless of whether one or more reactors are used for the reaction of the organic compound with hydroperoxide in the process of the present invention, the reaction conditions in each reactor are preferably selected so that the reaction mixture consists of a single phase and is liquid.

Zeolite catalysts which can be used for the purposes of the present invention are subject to no restrictions, as long as it is ensured that the catalysts catalyze the reaction of the organic compound with a hydroperoxide.

It is known that zeolites are crystalline aluminosilicates which have ordered channel and cage structures and have micropores which are preferably smaller than about 0.9 nm. The network of such zeolites is made up of $SiO_4$ and $AlO_4$ tetrahedra which are joined by shared oxygen bridges. An overview of the known structures may be found, for example, in W. M. Meier, D. H. Olson and Ch. Baerlocher, "Atlas of Zeolithe Structure Types", Elsevier, 5th edition, Amsterdam 2001.

Zeolites which contain no aluminum and in which the Si(IV) in the silicate lattice is partly replaced by titanium as Ti(IV) are also known. These titanium zeolites, in particular those having a crystal structure of the MFI type, and possible ways of preparing them are described, for example, in EP-A 0 311 983 or EP-A 405 978. In addition to silicon and titanium, such materials can further comprise additional elements such as aluminum, zirconium, tin, iron, cobalt, nickel, gallium, boron or small amounts of fluorine. In the zeolite catalysts which are preferably regenerated in the process of the present invention, the titanium of the zeolite can be partly or completely replaced by vanadium, zirconium, chromium or niobium or a mixture of two or more thereof. The molar ratio of titanium and/or vanadium, zirconium, chromium or niobium to the sum of silicon and titanium and/or vanadium and/or zirconium and/or chromium and/or niobium is generally in the range from 0.01:1 to 0.1:1.

Specific mention may be made of titanium-, germanium-, tellurium-, vanadium-, chromium-, niobium- and zirconium-containing zeolites having a pentasil zeolite structure, in particular the types which can be assigned X-ray-crystallographically to the ABW, ACO, AEI, AEL, AEN, AET, AFG, AFI, AFN, AFO, AFR, AFS, AFT, AFX, AFY, AHT, ANA, APC, APD, AST, ATN, ATO, ATS, ATT, ATV, AWO, AWW, BEA, BIK, BOG, BPH, BRE, CAN, CAS, CFI, CGF, CGS, CHA, CHI, CLO, CON, CZP, DAC, DDR, DFO, DFT, DOH, DON, EAB, EDI, EMT, EPI, ERI, ESV, EUO, FAU, FER, GIS, GME, GOO, HEU, IFR, ISV, ITE, JBW, KFI, LAU, LEV, LIO, LOS, LOV, LTA, LTL, LTN, MAZ, MEI, MEL, MEP, MER, MFI, MFS, MON, MOR, MSO, MTF, MTN, MTT, MTW, MWW, NAT, NES, NON, OFF, OSI, PAR, PAU, PHI, RHO, RON, RSN, RTE, RTH, RUT, SAO, SAT, SBE, SBS, SBT, SFF, SGT, SOD, STF, STI, STT, TER, THO, TON, TSC, VET, VFI, VNI, VSV, WIE, WEN, YUG, ZON structures and to mixed structures derived from two or more of the abovementioned structures. It is also conceivable to use titanium-containing zeolites having the ITQ4, SSZ-24, TTM-1, UTD-1, CIT-1 or CIT-5 structure in the process of the present invention. Further titanium-containing zeolites which may be mentioned are those of the ZSM-48 or ZSM-12 structure.

Titanium zeolites, in particular those having a crystal structure of the MFI type, and possible ways of preparing them are described, for example, in WO 98/55228, EP-A 0 311 983 or EP-A 0 405 978, whose relevant contents are fully incorporated by reference into the disclosure of the present patent application. Titanium zeolites having, for example, a crystal structure of the MWW type and possible ways of preparing them are described in WO 02/28774 A2 or in Wu et al., "Hydrothermal Synthesis of a novel Titanosilicate with MWW Topology", Chemistry Letters 2000, S. 774-775, whose relevant contents are fully incorporated by reference into the disclosure of the present patent application. For example, specific syntheses of Ti-MWW are described in examples 1 to 5 of WO 02/28774 A2.

In general, the zeolitic material which has been separated from its mother liquor is dried at generally from 80 to 160° C., preferably from 90 to 145° C. and particularly preferably from 100 to 130° C., and subsequently preferably calcined at generally from 400 to 750° C., preferably from 450 to 600° C. and particularly preferably from 490 to 530° C. In further embodiments of the process of the present invention, the zeolite is, after it has been separated off from the mother liquor, brought into contact with a water-containing composition. This contacting can likewise be carried out for the first time or repeated after the above-described drying procedure and/or the above-described calcination. In these cases, one or more of the above-described treatments for concentration or for separation can follow the contacting with the water-containing composition. As water-containing composition, preference is given, for example to water itself. It is likewise possible to use aqueous amine solutions in which the amine or amines present can be ammonia, an organic aliphatic amine or a quaternary ammonium hydroxide, where the nitrogen in these nitrogen compounds can bear, for example, methyl, ethyl or propyl radicals as alkyl radicals and two or more different alkyl radicals may also be bound to one nitrogen. The contacting with, preferably, water itself generally takes place at from room temperature to 750° C., preferably from 100 to 250° C. and particularly preferably from 120 to 175° C., and is preferably for a period of from 12 to 48 hours. This contacting very particularly preferably takes place in an autoclave.

If the zeolite has been dried and/or calcined after being separated off from the mother liquor and has subsequently been brought into contact with a water-containing composition, another drying and/or calcination step(s) can follow. This drying is generally carried out at from 80 to 160° C., preferably from 90 to 145° C. and particularly preferably from 100 to 130° C. The subsequent calcination which preferably occurs is generally carried out at from 400 to 750° C., preferably from 450 to 600° C., and particularly preferably from 490 to 530° C.

In addition to or instead of contacting with the water-containing composition, the zeolite can be washed with, for example, hydrogen peroxide solution, preferably low-sulfur hydrogen peroxide solution. It is likewise possible to treat the zeolitic material with alkali metal ions to convert the zeolites from the H form into the cationic form.

It is known that titanium zeolites having, for example, an MWW or MFI structure can be identified via a particular X-ray diffraction pattern and also via a lattice vibration band in the infrared region (IR) at about 960 cm$^{-1}$, and in this way differ from alkali metal titanates or crystalline and amorphous TiO$_2$ phases.

For the purposes of the present invention, particular preference is given to using titanium zeolites as zeolite catalysts.

Accordingly, the present invention also provides a process as described above in which the two or more different zeolite catalysts are titanium zeolite catalysts.

In a more preferred embodiment of the present invention, the zeolite catalysts used differ in their titanium content. Thus, the present invention encompasses, for example, embodiments in which one zeolite catalyst contains no titanium and at least one further zeolite catalyst is a titanium zeolite catalyst. In terms of the difference in the titanium content, preference is given to embodiments in which two titanium zeolite catalysts having different titanium contents are used.

If, for example, preferably two titanium zeolite catalysts having different titanium contents are used, these titanium zeolite catalysts have the chemical composition (I) or (II):

$$x.TiO_2(1-x).SiO_2 \qquad (I)$$

where $0.0001 \leq x \leq 0.2$, or

$$x.TiO_2 y.M_2O_3(1-x-2y).SiO_2 \qquad (II)$$

where $0.0001 \leq x \leq 0.2$ and $0.0001 \leq y \leq 0.1$ and M is at least one element from the group consisting of aluminum, boron, chromium, gallium, germanium and iron. The variables x and y are the respective mole fractions.

Further details of the zeolite structure types such as the structure type MFI, MEL or the structure type MWW may be found in the abovementioned reference W. M. Meier, D. H. Olson and Ch. Baerlocher "Atlas of Zeolite Structure Types", Elsevier, 5h. Edition, pp. 202 and 203, Amsterdam 2001.

Accordingly, the present invention also provides a process as described above in which the different zeolite catalysts differ in their titanium content.

For the purposes of the present invention, preference is given to using Ti zeolites having an MFI structure, MEL structure, MFI/MEL mixed structure or MWW structure. Further preference is given specifically to the Ti-containing zeolite catalysts generally referred to as "TS-1", "TS-2", "TS-3", and also Ti zeolites having a framework structure isomorphous with beta-zeolite. For the purposes of the present invention, very particular preference is given to zeolite catalysts having the TS-1 structure or the Ti-MWW structure.

In a likewise preferred embodiment, zeolite catalysts which differ in their structure type are used as different zeolite catalysts. For examples of possible structure types, reference may be made to the structure types mentioned above.

Examples of preferred zeolite catalysts which differ in their structure are zeolite catalysts of the TS-1 type and of the Ti-MWW type.

Accordingly, the present invention also provides a process as described above in which the titanium zeolite catalysts differ in respect of the titanium content or the zeolite structure or both the titanium content and the zeolite structure.

According to a further preferred process of the present invention, a titanium silicalite catalyst, especially preferably of structure type TS-1, is employed as catalyst. Different catalysts are therefore catalysts which have, e.g., a different content of titanium or different pore volumes or different specific surfaces or different contents of titanium and different pore volumes or different contents of titanium and different specific surfaces or different contents of titanium and different specific surfaces and different pore volumes. In case shaped catalyst bodies are produced from the titanium silicalite material in the process of the present invention, the different shaped bodies differ from each other with respect to, e.g., the type of the zeolite material or the titanium content or the SiO$_2$ content or the specific surface or the pore volume or the packed weight or the hardness such as the lateral pressure resistance or with respect to two or more of these parameters. Therefore, e.g., two different shaped bodies comprising different titanium silicalite materials or the same titanium silicalite material can be used in a single reactor. In case they comprise the same titanium silicalite material, the shaped bodies can differ with respect to the content of titanium silicalite and/or at least one of the above-mentioned parameters. In case they comprise different titanium silicalite materials, the shaped bodies can additionally differ with the respect to the content of titanium silicalite and/or at least one of the above-mentioned parameters.

Among the reactions of organic compounds with hydroperoxides which are possible in the process of the present invention, mention may be made by way of example of the following:

the epoxidation of olefins, e.g. the preparation of propene oxide from propene and H$_2$O$_2$ or from propene and mixtures which release H$_2$O$_2$ in situ;

hydroxylations, e.g. the hydroxylation of monocyclic, bicyclic or polycyclic aromatics to form monosubstituted, disubstituted or more highly substituted hydroxyaromatics, for example the reaction of phenol and H$_2$O$_2$ or of phenol and mixtures which release H$_2$O$_2$ in situ to give hydroquinone;

oxime formation from ketones in the presence of H$_2$O$_2$ or mixtures which release H$_2$O$_2$ in situ and ammonia (ammoximation), for example the preparation of cyclohexanone oxime from cyclohexanone;

the Baeyer-Villiger oxidation.

In the process of the present invention, preference is given to reacting organic compounds which have at least one C-C double bond. The present invention accordingly provides a process as described above in which the organic compound has at least one C-C double bond.

Examples of such organic compounds having at least one C-C double bond are the following alkenes:

ethene, propene, 1-butene, 2-butene, isobutene, butadiene, pentenes, piperylene, hexenes, hexadienes, heptenes, octenes, diisobutene, trimethylpentene, nonenes, dodecene, tridecene, tetradecene to eicosene, tripropene and tetrapropene, polytubadienes, polyisobutenes, isoprenes, terpenes, geraniol, linalool, linalyl acetate, methylenecyclopropane, cyclopentene, cyclohexene, norbornene, cycloheptene, vinylcyclohexane, vinyloxirane, vinylcyclohexene, styrene, cyclooctene, cyclooctadiene, vinylnorbornene, indene, tetrahydroindene, methylstyrene, dicyclopentadiene, divinylbenzene, cyclododecene, cyclododecatriene, stilbene, diphenylbutadiene, vitamin A, beta-carotene, vinylidene fluoride, allyl halides, crotyl chloride, methallyl chloride, dichlorobutene, allyl alcohol, methallyl alcohol, butenols, butenediols, cyclopentenediols, pentenols, octadienols, tridecenols, unsaturated steroids, ethoxyethene, isoeugenol, anethole, unsaturated carboxylic acids such as acrylic acid, methacrylic acid, crotonic acid, maleic acid, vinylacetic acid, unsaturated fatty acids such as oleic acid, linoleic acid, palmitic acid, naturally occurring fats and oils.

In the process of the present invention, preference is given to using alkenes containing from 2 to 8 carbon atoms. Particular preference is given to reacting ethene, propene and butene. Very particular preference is given to reacting propene.

Accordingly, the present invention also provides a process as described above in which an alkene is used as organic compound.

In the process of the present invention, at least one hydroperoxide is reacted with the organic compound. For the purposes of the present patent application, the term "hydroperoxide" refers to a compound of the formula ROOH. Details regarding the preparation of hydroperoxides and regarding hydroperoxides which can be used, inter alia, in the process of the present invention may be found in DE 198 35 907 A, whose relevant contents are incorporated by reference into the disclosure of the present patent application. Examples of hydroperoxides which can be used for the purposes of the present invention are, inter alia, tert-butyl hydroperoxide, ethylbenzene hydroperoxide, tert-amyl hydroperoxide, cumene hydroperoxide, cyclohexyl hydroperoxide, methylcyclohexyl hydroperoxide, tetrahydronaphthalene hydroperoxide, isobutylbenzene hydroperoxide, ethyl-naphthalene hydroperoxide, peracids such as peracetic acid and hydrogen peroxide. Mixtures of two or more hydroperoxides can also be used according to the present invention. Preference is given to using hydrogen peroxide as hydroperoxide in the process of the present invention, and further preference is given to using an aqueous hydrogen peroxide solution.

The present invention therefore also provides a process for the catalytic epoxidation of an alkene, preferably propene, by means of a hydroperoxide, preferably hydrogen peroxide, in at least one reactor using at least two different titanium zeolite catalysts, wherein at least two of the different zeolite catalysts are used physically separately from one another.

Physical separation is, for example, preferably achieved by using 2 serially coupled reactors and/or via a structured bed.

As solvent, it is in principle possible to use all solvents which are suitable for the respective reaction. Examples of preferred solvents include water,
alcohols, preferably lower alcohols, more preferably alcohols having less than 6 carbon atoms, for example methanol, ethanol, propanols, butanols and pentanols,
diols or polyols, preferably those having less than 6 carbon atoms,
ethers such as diethyl ether, tetrahydrofuran, dioxane, 1,2-diethoxyethane, 2-methoxyethanol,
esters such as methyl acetate or butyrolactone,
amides such as dimethylformamide, dimethylacetamide or N-methyl-pyrrolidone,
ketones such as acetone,
nitriles such as acetonitrile,
mixtures of two or more of the abovementioned compounds.

For the reaction of propene, particular preference is given to, for example, water, methanol, acetonitrile or mixtures of water and methanol or water and acetonitrile.

If a for example preferred process as described above is carried out in at least two reactors, it is possible, for example, to carry out the reaction in the presence of a first catalyst of the TS-1 type in a first reactor and in the presence of a second catalyst of the MWW type in a second reactor. In this case, preference is given, for example, to using methanol or a methanol/water mixture as solvent in the first reactor and acetonitrile or an acetonitrile/water mixture as solvent in the second reactor. It is likewise possible to use the catalyst of the MWW type in the first reactor and the catalyst of the TS-1 type in the second reactor. In each case, the MWW-Type catalyst is preferably a Ti-MWW catalyst.

Accordingly, the present invention also provides a process as described above in which the reaction is carried out in at least two reactors connected in series, where at least one titanium zeolite catalyst is used in at least one first reactor and at least one further titanium zeolite catalyst which differs from at least one of the titanium zeolite catalysts used in the first reactor is used in at least one second reactor.

According to the present invention, at least one intermediate separation can be carried out between the reactors connected in series according to the present invention. In this intermediate separation, preference is given, for example, to separating off at least one reaction product from the reaction mixture leaving the first reactor. Likewise, at least one by-product or at least one downstream product can be separated off. Likewise, a mixture comprising at least two of the abovementioned products can be separated off. In a preferred process in which an alkene is reacted with a hydroperoxide, preference is given to separating off unreacted hydroperoxide in such an intermediate separation. A two-stage reaction of alkene with a hydroperoxide according to the present invention using an intermediate separation therefore comprises, for example, the steps (A) to (C):

(A) reacting alkene with a hydroperoxide in at least one solvent or solvent mixture in the presence of a first zeolite catalyst to give a mixture comprising alkene oxide and unreacted hydroperoxide;
(B) separating off the unreacted hydroperoxide from the mixture resulting from (A);
(C) reacting the hydroperoxide which has been separated off in (B) with alkene in at least one solvent or solvent mixture in the presence of a second zeolite catalyst.

Accordingly, the present invention also provides a process as described above in which the reacted organic compound is separated off between at least two of the reactors connected in series.

The hydroperoxide used can be separated off in (B) using any suitable methods. The hydrogen peroxide which is, for example, preferably used is preferably separated off by distillation using one or more distillation columns, preferably one distillation column.

In a process according to the present invention comprising the steps (A) to (C), particular preference is given, for example, to reacting propene with hydrogen peroxide, where a catalyst of the TS-1 type is preferably used as zeolite catalyst and methanol is preferably used as solvent in (A) and a catalyst of the Ti-MWW type is preferably used as zeolite catalyst and acetonitrile is preferably used as solvent in (C).

In a process according to the present invention comprising the steps (A) to (C), particular preference is also given, for example, to reacting propene with hydrogen peroxide, where a catalyst of the Ti-MWW type is preferably used as zeolite catalyst and acetonitrile is preferably used as solvent in (A) and a catalyst of the TS-1 type is preferably used as zeolite catalyst and methanol is preferably used as solvent in (C).

The reaction conditions under which the reaction in the respective reactors is carried out can in principle be matched to the particular requirements of the process. The same applies, for example, to the precise size of individual catalyst compartments in the respective reactors and to the ratios of the geometries such as lengths, diameters or volumes of these compartments or the amounts of the catalysts used in the respective reactors and to the titanium contents of the different catalysts.

The reactors can, according to the present invention, be operated either in the suspension mode or in the fixed-bed mode. In suspension processes, particular preference is given in the case of the embodiment using reactors connected in series to a suspension of a first zeolite catalyst being used in a first reactor and a suspension of a second zeolite catalyst being used in a second reactor connected in series to the first reactor. It is likewise possible to operate at least one reactor in the suspension mode and at least one reactor in the fixed-bed mode.

In a preferred embodiment of the process of the invention, the reaction of the organic compound takes place in at least one fixed-bed reactor. If the reaction is carried out in a single reactor, this is a fixed-bed reactor, preferably a continuously operated fixed-bed reactor, more preferably a continuously operated fixed-bed tube reactor and very particularly preferably a continuously operated isothermal fixed-bed tube reactor. If the reaction takes place in, for example, two reactors connected in series, the first reaction preferably takes place in an isothermal fixed-bed tube reactor and the second reaction preferably takes place in an adiabatic fixed-bed tube reactor. Accordingly, the reactions of (A) and (C) are each carried out in a fixed-bed reactor and particularly preferably in a fixed-bed tube reactor. Very particular preference is given to carrying out the reaction of (A) in a isothermal fixed-bed reactor and the reaction of (C) in an adiabatic fixed-bed tube reactor.

Therefore, the present invention also provides a process, as described above, wherein at least one of the reactors used is operated in the fixed-bed mode.

After the reaction, the zeolite catalysts used in the process can be regenerated by one or more suitable methods either in the reactor or outside the reactor or both in the reactor and outside the reactor. In a preferred process, the zeolite catalysts are regenerated by means of a thermal treatment of the zeolite catalysts in the presence of a gas stream at above 120° C., preferably above 350° C. and in particular at from 400° C. to 650° C., in the reactor in which the reaction of propene is carried out, with the mass-based residence time of the gas stream over the catalyst during the thermal treatment being more than 2 hours, preferably in the range from 3 to 10 hours and particularly preferably in the range from 4 to 6 hours. The regeneration gas generally contains less than 20% by volume, preferably from 0.1 to 10% by volume, in particular from 0.1 to 5% by volume and more preferably from 0.1 to 2% by volume, of oxygen. Preference is given to using a mixture of air and appropriate volumes of nitrogen. The term "mass-based residence time" used in the context of the present invention refers to the ratio of the catalyst mass ($M_{cat}$) divided by the mass flow ($M_{gases}$) of the gas used in the regeneration. The regeneration is generally carried out so that the pressure drop over the reactor is not more than 4 bar, preferably not more than 3 bar and in particular not more than 2.5 bar.

As mentioned above, the reactors in which the reaction of the organic compound with hydrogen peroxide is carried out in a preferred embodiment of the present invention are equipped with shaped zeolite catalyst bodies. The shaped catalyst bodies can generally be produced by any suitable methods. As regards the specific step of the production of a shaped body, reference may be made to WO 98/55229 and DE 102 32 406.9, whose relevant contents are incorporated by reference into the disclosure of the present patent application.

Preference is given to admixing the zeolitic material which has been separated off from the mother liquor and, if appropriate, subjected to at least one treatment, e.g. washing, drying, calcination, contacting with a water-containing composition or treatment with hydrogen peroxide solution, with at least one binder. Further additives such as mixtures of water and at least one alcohol or at least one viscosity-increasing organic compound or at least one pore-forming compound, as are known from the prior art, can likewise be added.

As binder, it is possible to use essentially any compound which increases the cohesion between the particles of the zeolitic material. Preferred binders are binders selected from the group consisting of hydrated silica gel, silicic acid, silica gel, tetraalkoxysilicates, tetraalkoxytitanates, tetraalkoxyzirconates and mixtures of two or more thereof. Particular preference is given to tetramethoxysilicate, tetraethoxysilicate, tetrapropoxysilicate, tetrabutoxysilicate or silica sol. Particular preference is given to tetramethoxysilicate, tetraethoxysilicate and silica sol, with silica sol being very particularly preferred. Further binders are, for instance, aluminum oxide or calcium phosphate or mixtures of two or more of the binders mentioned.

Further binders are described in WO 98/55229 and DE 102 32 406.9, whose relevant contents are incorporated by reference into the disclosure of the present patent application.

The binders mentioned can be used either alone or as mixtures of two or more thereof. Further binders such as oxides of silicon, boron, phosphorus, zirconium and/or titanium can be used in addition.

The production of the shaped body according to the present invention is generally carried out using up to 80% by weight, preferably from 10 to 80% by weight, more preferably from 10 to 75% by weight and particularly preferably from 20 to 40% by weight, of binder, based on the total weight of the shaped body.

In a further preferred embodiment of the process of the present invention, at least one pore former is added to the zeolitic material. Preference is in this case given to using polymers, more preferably polymers which can be dispersed, emulsified or suspended in water or aqueous solvents. This polymer or polymers is/are preferably selected from the group consisting of vinyl polymers such as polystyrene, polyacrylates, polymethacrylates, polyolefins, polyamides and polyesters. After production of the shaped bodies, these pore-forming polymers are removed from the shaped body by calcination at appropriate temperatures. If polymers are added as pore formers, they are added in a proportion of generally from 5 to 50% by weight, preferably from 7 to 35% by weight and particularly preferably from 10 to 20% by weight, in each case based on the total weight of the inorganic components of binder and zeolite.

Further preference is given to adding at least one extrusion aid. As extrusion aid, it is possible to use essentially any compound which leads to an improvement in the mixing, kneading or flow properties. Preference is given to organic hydrophilic polymers such as cellulose, cellulose derivatives, for example alkylcelluloses, starch, polyacrylates, polymethacrylates, polyvinyl alcohol, polyvinylpyrrolidone, polyisobutene or polytetrahydrofuran. According to the present invention, these compounds are used because they increase the mechanical stability of the shaped bodies, preferably during shaping and drying and during subsequent use as shaped catalyst bodies. These compounds are removed from the shaped body by calcination at appropriate temperatures.

Further additives are described in EP 0 389 041 A, EP 0 200 260 A and WO 95/19222, whose relevant contents are incorporated by reference into the disclosure of the present patent application.

In a preferred embodiment of the process of the present invention, the addition of the binder or binders to the zeolitic material is followed by addition of the organic viscosity-increasing compound or compounds and homogenization of the resulting composition in a kneading apparatus or extruder for from 10 to 180 minutes. This homogenization is carried out at temperatures which are generally about 10° C. below the boiling point of the extrusion aid. The pressure employed is generally approximately ambient pressure or slightly superatmospheric pressure.

In a further preferred embodiment of the process of the present invention, firstly the pore-forming compound or compounds and subsequently the binder or binders are added to the zeolitic material during the kneading procedure. After these have been added, the water-containing composition or compositions, preferably water, is/are added in one or more steps. In a further preferred embodiment, firstly the pore-forming compound or compounds and subsequently part of the binder or binders are added during kneading, and part of the water-containing composition or compositions, preferably water, is then added in one or more steps. The remainder of the binder is then added, followed by the remainder of the water-containing composition or compositions, preferably water, in one or more steps.

Preference is given to adding silica sol and/or a polystyrene dispersion and/or cellulose and/or a cellulose derivative such as an alkylcellulose and/or polyethylene oxide and/or water to the zeolitic material. For example, the zeolitic material is preferably admixed with silica sol, a polystyrene dispersion, methylcellulose and water and then homogenized by kneading in a suitable apparatus.

Accordingly, the present invention also provides a process as described above in which the production of the shaped body in (b) comprises at least the step (aa):

(aa) kneading the porous oxidic material obtained in (a) with addition of at least one binder or at least one extrusion aid or at least one pore former or a water-containing composition or a mixture of two or more thereof.

In a more preferred embodiment, the composition which has been kneaded as described above is shaped to produce a shaped body. This can generally be carried out by any suitable methods. In the process of the present invention, the shaped bodies are preferably produced by means of an extruder. Preference is given to producing extrudates having a diameter in the range from 1 to 10 mm, more preferably from 1 to 5 mm and particularly preferably from 1 to 2 mm.

Shaping can be carried out at ambient pressure or at a pressure above ambient pressure, generally a pressure in the range from 1 to 700 bar. Furthermore, shaping can be carried out at ambient temperature or at a temperature higher than ambient temperature, generally at a temperature in the range from 20 to 300° C. Shaping can also be carried out in a controlled atmosphere, generally an inert gas atmosphere, a reducing atmosphere or an oxidizing atmosphere.

The individual shaped bodies can in general be separated off from the strand of molding composition leaving the extruder by all possible methods. The paste-like strand of molding composition in the extruder is particularly preferably separated off by bringing the paste-like molding composition into contact with at least one stream comprising at least one fluid medium to divide it. The fluid medium is more preferably a gas or a liquid, particularly preferably essentially air. Preference is likewise given to the strand of the paste-like molding composition being divided periodically. This method makes it possible to produce shaped bodies which have a higher bulk density than is obtained by the mechanical separation methods of the prior art. This is particularly advantageous when the shaped bodies are used in fixed-bed reactors.

Accordingly, the present invention also provides a process as described above in which the production of the shaped body in (b) comprises at least the steps (aa) and (bb):

(aa) kneading the porous oxidic material obtained in (a) with addition of at least one binder or at least one extrusion aid or at least one pore former or a water-containing composition or a mixture of two or more thereof;

(bb) shaping the kneaded mixture obtained in (aa) to give at least one shaped body.

The shaped bodies are then preferably dried at from 30 to 140° C., preferably from 60 to 135° C. and particularly preferably from 90 to 130° C., with the drying times generally being in the range from 1 to 20 h, preferably from 2 to 10 h and particularly preferably from 3 to 5 h. The heating rates employed are generally from 0.5 to 5° C./min, preferably from 1 to 4° C./min and particularly preferably from 1.5 to 3° C./min.

Accordingly, the present invention also provides a process as described above in which the production of the shaped body in (b) comprises at least the steps (aa) to (cc):

(aa) kneading the porous oxidic material obtained in (a) with addition of at least one binder or at least one extrusion aid or at least one pore former or a water-containing composition or a mixture of two or more thereof;

(bb) shaping the kneaded mixture obtained in (aa) to give at least one shaped body;

(cc) drying the shaped body obtained in (bb).

The dried shaped bodies are then preferably calcined at from 400 to 800° C., preferably from 425 to 600° C. and particularly preferably from 450 to 500° C., with the calcination times generally being in the range from 1 to 20 h, preferably from 2 to 10 h and particularly preferably from 3 to 7 h. The heating rates employed are generally from 0.25 to 2° C./min, preferably from 0.5 to 1.5° C./min and particularly preferably from 0.75 to 1.25° C./min. Very particular preference is given to calcining the dried shaped body under air and/or lean air.

Accordingly, the present invention also provides a process as described above in which the production of the shaped body in (b) comprises at least the steps (aa) to (dd):

(aa) kneading the porous oxidic material obtained in (a) with addition of at least one binder or at least one extrusion aid or at least one pore former or a water-containing composition or a mixture of two or more thereof;

(bb) shaping the kneaded mixture obtained in (aa) to give at least one shaped body;

(cc) drying the shaped body obtained in (bb);

(dd) calcining the dried shaped body obtained in (cc).

Before or after the drying and/or calcination of the shaped bodies obtained in (bb), they can, as described above with regard to the zeolitic material, be brought into contact with a water-containing composition. If the dried and/or calcined shaped bodies are brought into contact with the water-containing composition, this is preferably followed by another drying and/or calcination step(s) which is/are carried out as described under (cc) and/or (dd).

Accordingly, the present invention also provides a shaped catalyst body as described above which is obtainable by a process comprising the step (aa) or the steps (aa) and (bb) or the steps (aa), (bb) and (cc) or the steps (aa), (bb), (cc) and (dd), wherein the shaped body is brought into contact with a water-containing composition after step (bb) or step (cc) or step (dd).

EXAMPLES

All examples were carried out in a tube bundle reactor having 5 parallel tubes (each having a length of 12 m and a diameter of 40 mm). Each tube contained 5.7 kg of catalyst bed. As feed into the epoxdiation reactor, the following mixture was used in all of the 3 experiments:

| compound | flow rate/(kg/h) | % |
|---|---|---|
| propene (chemical grade) | 11.3 | 11 |
| methanol (98%) | 74.26 | 72 |
| $H_2O_2$ (40%) | 17 | 17 |

The fixed-bed reactor was passed through from the bottom to the top. The reactor was cooled with cooling water via the jacket.

Example 1

Use of a Single Catalyst

Comparative Example

The fixed-bed tube reactor was filled with shaped catalyst bodies. As catalytically active component, the shaped bodies comprised a zeolite material (titanium silicalite of structure type TS-1). The zeolite material had a titanium content, calculated as $TiO_2$, of 2.0 percent by weight. The molar ratio of $SiO_2/TiO_2$ was 59.

The shaped catalyst bodies comprising this zeolite had a titanium content, calculated as $TiO_2$, of 1.2 percent by weight, and a $SiO_2$ content of 98.8 percent by weight. The shaped bodies were extrudates with a diameter of 1.5 mm and a packed weight of 470 g/l. The lateral pressure resistance was 9.1 N, determined with a Zwick measuring apparatus, model BZ2.5/TS1S. The pre-power was 0.5 N, the pre-power velocity was 10 mm/min, and the testing velocity was 1.6 mm/min. The total pore volume of the shaped bodies was 0.73 ml/g, determined according to DIN 66133, the specific surface was 397 m$^2$/g, determined according to DIN 66131.

Epoxidation at 20 bar, a peak temperature of about 56° C. and a cooling water temperature of 45° C. gave a yield of propylene oxide of 91% with respect to $H_2O_2$ employed.

Example 2

Use of Two Different Catalysts

The fixed-bed tube reactor was filled with shaped catalyst bodies. As catalytically active component, the shaped bodies comprised a zeolite material (titanium silicalite of structure type TS-1). Two different types of shaped bodies were used.

As lower layer of the reactor, 4.0 kg of the following shaped bodies were filled in:

The zeolite material comprised in the shaped bodies had a titanium content, calculated as $TiO_2$, of 2.3 percent by weight. The molar ratio of $SiO_2/TiO_2$ was 52. The pore volume of the zeolite material, determined according to DIN 66134, was 0.497 ml/g, the specific surface, determined according to DIN 66131, was 508 m$^2$/g.

The shaped catalyst bodies comprising this zeolite had a titanium content, calculated as $TiO_2$, of 2.0 percent by weight, and a $SiO_2$ content of 98.0 percent by weight. The shaped bodies were extrudates with a diameter of 1.5 mm and a packed weight of 498 g/l. The lateral pressure resistance of the shaped bodies was 27 N, determined with a Zwick measuring apparatus, model BZ2.5/TS1S. The pre-power was 0.5 N, the pre-power velocity was 10 mm/min, and the testing velocity was 1.6 mm/min. The total pore volume of the shaped bodies was 0.78 ml/g, determined according to DIN 66133, the specific surface was 190 m$^2$/g, determined according to DIN 66131. Subsequently after their preparation and prior to their use in the process, the shaped bodies were contacted with water for 12 h at a temperature of 130° C.

As upper layer of the reactor, 1.7 kg of the shaped bodies according to example 1 were filled in.

The catalyst layers directly adjoined and were not separated from each other by a physical spacer.

Epoxidation at 20 bar, a peak temperature of about 56° C. and a cooling water temperature of 45° C. gave a yield of propylene oxide of 92.2% with respect to $H_2O_2$ employed.

Example 3

Use of Two Different Catalysts

The fixed-bed tube reactor was filled with shaped catalyst bodies. As catalytically active component, the shaped bodies comprised a zeolite material (titanium silicalite of structure type TS-1). Two different types of shaped bodies were used.

As lower layer of the reactor, 5.0 kg of the following shaped bodies were filled in:

The zeolite material comprised in the shaped bodies had a titanium content, calculated as $TiO_2$, of 2.3 percent by weight. The molar ratio of $SiO_2/TiO_2$ was 52. The pore volume of the zeolite material, determined according to DIN 66134, was 0.497 ml/g, the specific surface, determined according to DIN 66131, was 508 m$^2$/g.

The shaped catalyst bodies comprising this zeolite had a titanium content, calculated as $TiO_2$, of 2.0 percent by weight, and a $SiO_2$ content of 98.0 percent by weight. The shaped bodies were extrudates with a diameter of 1.5 mm and a packed weight of 498 g/l. The lateral pressure resistance of the shaped bodies was 17 N, determined with a Zwick measuring apparatus, model BZ2.5/TS 1S. The pre-power was 0.5 N, the pre-power velocity was 10 mm/min, and the testing velocity was 1.6 mm/min. The total pore volume of the shaped bodies was 0.88 ml/g, determined according to DIN 66133, the specific surface was 313 m$^2$/g, determined according to DIN 66131. Subsequently after their preparation and prior to their use in the process, the shaped bodies were contacted with water for 36 h at a temperature of 140° C.

As upper layer of the reactor, 0.7 kg of the shaped bodies according to example 1 were filled in.

The catalyst layers directly adjoined and were not separated from each other by a physical spacer.

Epoxidation at 20 bar, a peak temperature of about 55° C. and a cooling water temperature of 43° C. gave a yield of propylene oxide of 93.4% with respect to $H_2O_2$ employed.

We claim:
1. A process for the catalyzed reaction of an organic compound having at least one C-C double bond with a hydroperoxide in a reaction mixture present within at least one reactor, wherein said process comprises adding at least two different titanium zeolite catalysts to the reaction mixture, wherein the different titanium zeolite catalysts are physically separated from one another, and wherein each of the titanium zeolite catalysts differ from one another with respect to titanium content, zeolite structure, or both the titanium content and the zeolite structure.

2. The process according to claim 1, wherein at least one titanium zeolite catalyst has a crystal structure of the MWW type, and at least one titanium zeolite catalyst has a crystal structure of the MFI type.

3. The process according to claim 1, wherein at least one reactor is operated in a fixed-bed mode.

4. The process according to claim 1, wherein the organic compound is an alkene.

5. The process according to claim 1, wherein the organic compound is an alkene selected from the group consisting of ethene, propene and butene.

6. The process according to claim 1, wherein the hydroperoxide is one or more hydroperoxides selected from the group consisting of tert-butyl hydroperoxide, ethylbenzene hydroperoxide, tert-amyl hydroperoxide, cumene hydroperoxide, cyclohexyl hydroperoxide, methylcyclohexyl hydroperoxide, tetrahydronaphthalene hydroperoxide, isobutylbenzene hydroperoxide, ethyl-naphthalene hydroperoxide, peracetic acid and hydrogen peroxide.

7. The process according to claim 1, wherein the catalyzed reaction is carried out in a single reactor.

8. The process according to claim 7, wherein at least one titanium zeolite catalyst has a crystal structure of the MWW type, and at least one titanium zeolite catalyst has a crystal structure of the MFI type.

9. The process according to claim 7, wherein at least one reactor is operated in a fixed-bed mode.

10. The process according to claim 9, wherein at least one titanium zeolite catalyst has a crystal structure of the MWW type, and at least one titanium zeolite catalyst has a crystal structure of the MFI type.

11. The process according to claim 9, wherein the organic compound is an alkene.

12. The process according to claim 9, wherein the organic compound is an alkene selected from the group consisting of ethene, propene and butene.

13. The process according to claim 9, wherein the hydroperoxide is one or more hydroperoxides selected from the group consisting of tert-butyl hydroperoxide, ethylbenzene hydroperoxide, tert-amyl hydroperoxide, cumene hydroperoxide, cyclohexyl hydroperoxide, methylcyclohexyl hydroperoxide, tetrahydronaphthalene hydroperoxide, isobutylbenzene hydroperoxide, ethyl-naphthalene hydroperoxide, peracetic acid and hydrogen peroxide.

14. The process according to claim 1, wherein the catalyzed reaction is carried out in at least two reactors coupled together in series, wherein at least one titanium zeolite catalyst is present within at least one reactor, wherein at least one other titanium zeolite catalyst is present within at least one other reactor, and wherein at least one of the titanium zeolite catalysts differs from at least one of the other titanium zeolite catalysts with respect to titanium content, zeolite structure, or both the titanium content and the zeolite structure.

15. The process according to claim 14, wherein at least one titanium zeolite catalyst has a crystal structure of the MWW type, and at least one other titanium zeolite catalyst has a crystal structure of the MFI type.

16. The process according to claim 14, wherein at least one of the reactors is operated in a fixed-bed mode.

17. The process according to claim 16, wherein at least one titanium zeolite catalyst has a crystal structure of the MWW type, and at least one other titanium zeolite catalyst has a crystal structure of the MFI type.

18. The process according to claim 16, wherein the organic compound is an alkene.

19. The process according to claim 16, wherein the organic compound is an alkene selected from the group consisting of ethene, propene and butene.

20. The process according to claim 16, wherein the hydroperoxide is one or more hydroperoxides selected from the group consisting of tert-butyl hydroperoxide, ethylbenzene hydroperoxide, tert-amyl hydroperoxide, cumene hydroperoxide, cyclohexyl hydroperoxide, methylcyclohexyl hydroperoxide, tetrahydronaphthalene hydroperoxide, isobutylbenzene hydroperoxide, ethyl-naphthalene hydroperoxide, peracetic acid and hydrogen peroxide.

* * * * *